United States Patent [19]
Rouillard et al.

[11] Patent Number: 5,824,320
[45] Date of Patent: Oct. 20, 1998

[54] COSMETIC OR PHARMACEUTICAL COMPOSITIONS CONTAINING, AS ACTIVE INGREDIENT, MANGIFERINE OR ITS DERIVATIVES, IN PURE FORM OR IN PLANT EXTRACTS

[75] Inventors: Francoise Rouillard, Longjumeau; Annabelle Josse, Thiais; Jean-Renaud Robin, Saint-Denis, all of France

[73] Assignee: Laboratories de Biologie Vegetale Yves Rocher, La Gacilly, France

[21] Appl. No.: 682,616

[22] PCT Filed: Nov. 23, 1995

[86] PCT No.: PCT/FR95/01552

§ 371 Date: Sep. 18, 1996

§ 102(e) Date: Sep. 18, 1996

[87] PCT Pub. No.: WO96/16632

PCT Pub. Date: Jun. 6, 1996

[30] Foreign Application Priority Data

Nov. 25, 1994 [FR] France .................................. 94 14176
Mar. 24, 1995 [FR] France .................................. 95 03513
Jun. 22, 1995 [FR] France .................................. 95 07508

[51] Int. Cl.$^6$ ...................................................... A61K 7/48
[52] U.S. Cl. ........................... 424/401; 424/61; 424/701; 514/455; 514/844; 514/846; 514/937; 514/944
[58] Field of Search ................................... 424/401, 701, 424/61; 514/455, 844, 846, 937, 944

[56] References Cited

U.S. PATENT DOCUMENTS 4,217,341   8/1980   Suddick et al. ............................ 424/48

FOREIGN PATENT DOCUMENTS 689583    4/1967   Belgium .
2 486 941   1/1982   France .
31 41 970   5/1983   Germany .
2 102 290   2/1983   United Kingdom .

OTHER PUBLICATIONS

S. Guha et al., "Activation of Peritoneal Macrophages by Mangiferin, a Naturally Occurring Xanthone", *Phytotherapy Research*, vol. 7, No. 2, 1993, pp. 107–110.

T. Sato et al., "Mechanism of Antioxidant Action of Pueraria Glycoside (PG)—1 (an Isoflavonoid) and Mangiferin (a Xanthonoid)", *Chemical Pharmaceutical Bull.*, vol. 40, No. 3, 1992, pp. 721–724.

*Primary Examiner*—Jyothsan Venkat
*Attorney, Agent, or Firm*—Young & Thompson

[57] ABSTRACT

A cosmetic or pharmaceutical composition including, as the active ingredient, a compound of general formula (I), wherein $R_1$, $R_2$, $R_3$, $R_4$, $R_5$, $R_6$, $R_7$ and $R_8$ are selected from —H, —OH, —OCH$_3$ and a glucosyl radical, or a pharmaceutically acceptable salt thereof.

13 Claims, 6 Drawing Sheets

COSMETIC OR PHARMACEUTICAL COMPOSITIONS CONTAINING, AS ACTIVE INGREDIENT, MANGIFERINE OR ITS DERIVATIVES, IN PURE FORM OR IN PLANT EXTRACTS

This application is a 371 of PCT/FR95/01552 filed Nov. 23, 1995.

FIELD OF THE INVENTION

The invention relates to cosmetic or pharmaceutical compositions containing, as active ingredient, mangiferine (or its derivatives) of natural origin or obtained by chemical, enzymatic or biotechnological synthesis, as well as to compositions containing, as active ingredient, a mangiferine-containing plant extract, in particular an Aphloia or Mangifera leaf extract.

These compositions can be used especially to protect the skin against ultraviolet radiation and skin ageing and to enhance its structural quality.

BACKGROUND OF THE INVENTION

Mangiferine is a C-glucoside of 1,3,6,7-tetrahydroxy xanthone. It is also called aphloiol (Billet and al., 1965). This molecule, as well as its derivatives (methylated, O-glucosyl or isomangiferine derivatives), are present naturally in a number of plants, but it is mangiferine that is the most widely distributed C-glucoside xanthone (Hostettmann, 1977), and more particularly among the angiosperms.

It has the chemical structure below:

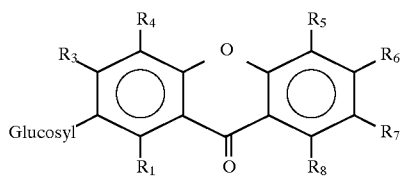

where $R_1=R_3=R_6=R_7=OH$ and $R_4=R_5=R_8=H$.

Isomangiferine, which has the structure below:

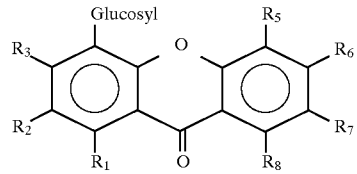

where $R_1=R_3=R_6=R_7=OH$ and $R_2=R_5=R_8=H$, also exists naturally. Its derivatives of natural origin can have O-methyl (—OCH$_3$) or glucosyl (—C$_6$H$_{11}$O$_6$) groups at the $R_1$, $R_3$, $R_6$ or $R_7$ positions.

All the compounds formed by mangiferine and its derivatives correspond to the following general formula (I):

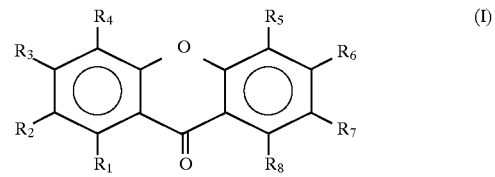

where $R_1$, $R_2$, $R_3$, $R_4$, $R_5$, $R_6$, $R_7$ are selected from —H, —OH, —OCH$_3$ and a glucosyl radical.

The compounds of formula I can be obtained by various means:

1) extraction from plant materials. Mangiferine and its derivatives are present naturally in various plants, including in particular the species indicated in the following table:

| CLASS | SUBCLASS | ORDER | FAMILY | SPECIES |
|---|---|---|---|---|
| Filices | Leptosporangiatae | Filicales | Polypodiaceae | *Athyrium mesosorum* |
| Dicotyledoneae | Archichlamydeae | Guttiferales | Guttiferae | *Hypericum acutum* |
|  |  |  |  | *H. chinense* |
|  |  |  |  | *H. humifusum* |
|  |  |  |  | *H. montanum* |
|  |  |  |  | *H. nummularium* |
|  |  |  |  | *H. pulchrum* |
|  |  | Rosales | Leguminosae | *Hedysarum obscurum* |
|  |  | Rutales | Malphighiaceae | *Hiptage madablota* |
|  |  | Sapindales | Anacardiaceae | *Mangifera indica* |
|  |  | Celastrales | Hippocrateaceae | *Salacea prunoides* |
|  |  | Violales | Flacourtiaceae | *Flacourtia indica* |
|  |  |  |  | *Aphloia theaeformis* |
|  |  |  |  | *A. madagascariensis* |
|  | Sympetalae | Ebenales | Sapotaceae | *Madhuca utilis* |
|  |  | Tubiflorae | Convolvulacea | *Cuscuta reflexa* |
| Monocotyledoneae |  | Liliiflorae | Liliceae | *Anemarrhena rhizoma* |
|  |  |  |  | *Smilax glycyphylla* |
|  |  |  | Iridaceae | All spp. of pogoniris section |
|  |  |  |  | *Iris pseudacorus* |
|  |  |  |  | *Iris dichotoma* |
|  |  |  |  | *Belamcanda chinensis* |
|  |  |  |  | *Crocus aureus* |
|  |  | Graminales | Gramineae | *Cymbopogon afronardus* |

The species Aphloia and Mangifera are plants whose leaves are high in mangiferine.

Aphloia is a shrub which is completely glabrous, 3 to 4 m high, native to the East coast of Madagascar and the neighbouring islands (Réunion, Mauritius, Seychelles, Comoro). The alternate leaves are simple, lanceolate, dentate to a greater or lesser extent along the edges except at the base and are not stipulate.

The solitary hermaphrodite flowers, in the form of pauciflores cymes, are apetalous. They possess 4 to 6 imbricated sepals; the innermost are petaloid.

The fruits are berries which are white when mature.

The leaves of this plant are known for their diuretic, veinotonic and cicatrizant properties which have caused them to be used as infusion in traditional medicine.

Mangifera, and in particular *Mangifera indica*, belongs to the Anacardiaceae family. The genous mangifera is characterized by the following common characters: trees with leaves which are alternate, petiolate, entire/coriaceous with terminal inflorescences in the form of panicles. The fruits are drupes.

This genus comprises sixty-two arborescent species, of which 16 species bear fruit.

The species *Mangifera indica* L. in particular is an upright tree with a more or less spreading habit 9 to 30 m high, which is always green. This species currently comprises about 1000 varieties. The fruit-producing Mangifera species are very widespread. *Mangifera indica* is found in particular in Asia, Central and South America and in Tropical Africa.

Traditionally, the Mangifera fruit is consumed by the local populations who also use other parts of the tree for various uses: *Mangifera indica* in particular is commonly used to treat the populations: infusions of the bark to treat leukorrhea, haemorrhages and dysentery. The leaves are used as a decoction for voice loss, and for diabetes. The ash of the leaves is also used on burns.

The compounds of formula I are for example obtained by purifying extracts of all or part of these plants, according to any extraction and purification process (for example, extraction by a polar solvent such as water, an alkanol, or mixtures of these solvents, followed by purification by crystallization or any other process known to persons skilled in the art). Some of these processes are described for example in the patent published under the number FR-A-2,486,941.

2) By a chemical or enzymatic route (processes described, inter alia, in two articles: Bhatia-V-K and al., Tetrahedron lett.(14), p. 1741–2 and Nott-P-E, Phytochemistry, vol 6 (11); p. 1597–9).

3) By any biotechnical route: It is possible to envisage the culture of Mangifera cells, as calluses on solid supports or in fermenters, or in the form of protoplasts. However, it is also possible to envisage using the bioconversion of precursors of mangiferine or of its derivatives by microorganisms (for example yeasts, bacteria and the like) and its production by extraction from these microorganisms, or by excretion into the culture medium.

The mangiferine (or its derivatives) can be used at various levels of purity, alone or as a mixture.

The dry purified mangiferine exists in the form of prismatic needles which are yellow in colour. It has no odour or taste.

It is very sparingly soluble in cold water and is soluble in alkaline liquids. Its solubilization is due to the formation of salts by the phenolic "OH" groups and mangiferine (or its derivatives) can be used in free form or in the form of its salts.

The authors of the present invention have studied the biological properties of mangiferine (and its derivatives) in a pure form or in the form of plant extracts. In particular, they studied the activities of Aphloia or Mangifera extracts whose leaves are high in mangiferine.

SUMMARY OF THE INVENTION

The inventors have now discovered that mangiferine and its derivatives, in purified form or contained in plant extracts, in particular the extracts of Aphloia or Mangifera leaf, possess highly pronounced anti-ultraviolet (UV), anti-collagenase and anti-elastase activities. These compounds of formula I also have anti-free radical and anti-tyrosinase properties. They are therefore particularly useful in cosmetic or pharmaceutical compositions intended for the protection of the epidermis against ultraviolet rays, for enhancing the structural quality of the skin and for providing help in combatting biological and/or actinic skin ageing.

Consequently, the subject of the invention is cosmetic or pharmaceutical compositions comprising, as active ingredient, a compound of the following general formula I:

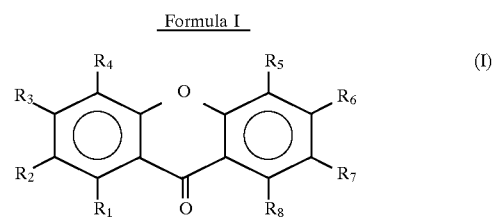

Formula I (I)

where $R_1$, $R_2$, $R_3$, $R_4$, $R_5$, $R_6$, $R_7$, $R_8$ are selected from —H, —OH, —OCH$_3$ and a glucosyl radical or one of its pharmaceutically acceptable salts.

According to an advantageous variant, the compositions of the present invention comprise, as active ingredient, a compound of formula I, where $R_1$, $R_3$, $R_6$, $R_7$, are chosen from —H, —OH, —OCH$_3$ and a glucosyl radical, and $R_2=R_5=R_8=$H and $R_4$ is a glucosyl radical, or $R_2$ is a glucosyl radical and $R_4=R_5=R_8=$—H.

Still more preferably, $R_1=R_3=R_6=R_7=$OH, $R_2$ is a glucosyl radical and $R_4=R_5=R_8=$—H.

According to one advantageous embodiment, the compositions according to the invention comprise a compound of the formula I obtained from a plant extract.

These compositions preferably comprise, depending on the compound chosen, proportions ranging from 0.01 to 50% and still more preferably from 0.01 to 10% by weight of this compound in dry form.

The subject of the invention is also cosmetic or pharmaceutical compositions comprising an extract of Aphloia or Mangifera leaves as active ingredient, especially extracts obtained by extraction with polar solvents.

The compositions comprising an Aphloia or Mangifera extract generally comprise from 0.1 to 20% by weight of dry extract relative to the total weight of the composition. The proportion of extract may, however, range up to 50% in the case of a liquid extract.

The compositions according to the invention have a photoprotective effect on the skin, the lips or the hair. They are generally intended to enhance the structural quality of the skin, or to combat skin ageing.

The compositions according to the invention are provided preferably in the form of a simple Oil/Water or Water/Oil emulsion, multiple emulsions or microemulsions, aqueous or aqueous-alcoholic gels, oils, aqueous or aqueous-alcoholic lotions, a cream, a stick, a shampoo or a conditioner.

The subject of the invention is also a method of aesthetic treatment consisting in applying to the skin, the hair or the lips any one of these cosmetic compositions.

Its subject is in addition the use of a compound of formula I (mangiferine or its derivatives) or of an extract of Aphloia or Mangifera leaves for the manufacture of pharmaceutical or cosmetic compositions with photoprotective, anti-collagenase and anti-elastase, anti-free radical and anti-tyrosinase action.

BRIEF DESCRIPTION OF THE DRAWINGS

The properties of the Aphloia and Mangifera extracts as well as those of the purified mangiferine will be described below, these properties being illustrated by FIGS. 1 to 7b, in which.

I—APHLOIA EXTRACTS

The Aphloia extract is obtained from any Aphloia subspecies, for example *Aphloia theaformis* (Vahl) Benn, and *Aphloia madagascariensis* Clos.

The principal constituents currently identified in the extract of Aphloia leaves of the invention are:

a C-glucosyltetrahydroxyxanthan (Aphloiol)

Flavenoids

Tannins

Three triterpene glucosides (glucoside ester of tormentic acid and of 23-hydroxytormentic acid and glucoside ester of 6-β-hydroxytormentic acid).

It is free of alkaloid substances.

The Aphloia extracts can be obtained by subjecting the fresh or dry Aphloia leaves to extraction by a polar solvent, especially by a solvent such as water, an alkanol (for example ethanol, methanol), propylene glycol, butylene glycol or a mixture of these solvents. It is possible, for example, to use an alkanol/water mixture or a propylene glycol/water mixture.

The weight of the solvent used is preferably equal to 2 to 20 times the weight of the leaves expressed in terms of the dry weight. The extraction is advantageously carried out, with stirring, at a temperature of between 10° C. and the boiling temperature of the solvent. The duration of the extraction is preferably from 15 minutes to 5 hours.

The extractive solutions are optionally concentrated, the concentrates obtained are optionally dried by means known to persons skilled in the art (vacuum oven, microwave oven and the like).

Example of Aphloia Extract

The extract studied was obtained in the following manner:

6% (w/w) of dry leaves from *Aphloia theaformis* of Madagascan origin, coarsely ground, are brought into contact, with stirring and at 55° C., with a propylene glycol/water mixture (40/60). The extraction takes place for 1 h 30 min. The plant is separated by filtration on a cloth (55 μm). The extract is then filtered on a plate filter (5 μm).

The pH of the extract is around 5.5 and its dry extract between 0.8 and 1.3%.

Photoprotective Effect

Figure 1A:
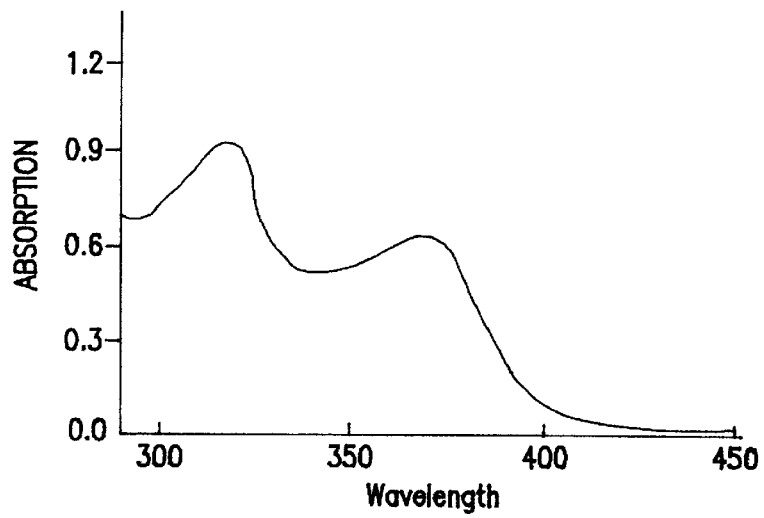
FIG. 1a represents the UV light absorption spectrum as a function of the wavelength for an Aphloia extract.

The Aphloia extract described above exhibits a UV absorption spectrum which is very useful for an application for protecting against solar erythema, with a maximum at around 320 nm, corresponding to UVB rays and another at around 360 nm, corresponding to the zone of UVA rays, as represented in Figure 1a.

Moreover, the absence of phototoxicity was verified.

Taking into account the safety of this extract, the resistance of the extract to irradiation, that is to say its photostability, compared with those of synthetic screening agents already marketed, such as for example octylmethoxy-cinnamate (PARSOL MCX, Givaudan, Basle, Switzerland) was verified.

A sunscreen is a molecule which, by definition, absorbs highly energetic ultraviolet radiations. Thus excited, it is capable of losing its energy, either by emitting a radiation of higher wavelength, or by undergoing intramolecular transformations.

These rearrangements modify its physico-chemical properties and in particular its ability to absorb light in the zone of the spectrum considered.

The extract was therefore subjected to a continuous radiation whose spectrum is comparable to that of sunlight and has a controllable energy level, emitted by a xenon lamp. The variation of the absorption spectrum was monitored over time and the half-life time measured (duration of irradiation necessary for a 50% loss of absorption at a fixed wavelength).

Figure 2A:
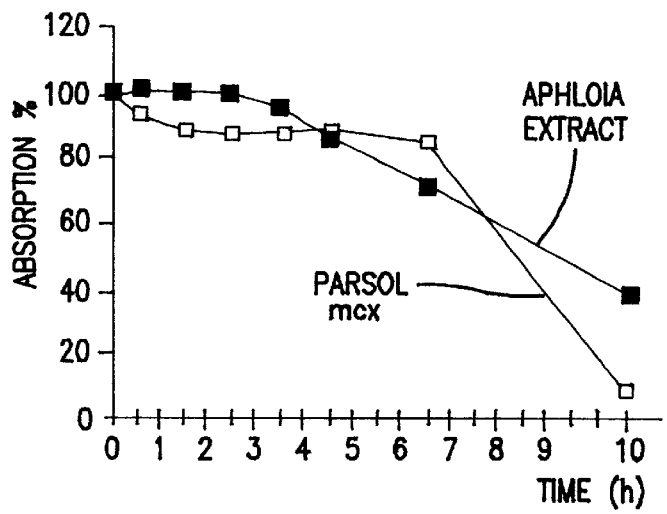
FIG. 2a represents the photostability as a function of the irradiation time for an Aphloia extract compared with a commercially available sunscreen, Parsol MCX.

As represented in FIG. 2a, the Aphloia extract, compared with PARSOL MCX under the same conditions, proved equally resistant to irradiation with a very similar half-life time.

Finally, the Aphloia extract prepared according to the process described above was tested in a cosmetic composition in order to evaluate its protection value SPF, according to the SOLATEX method, a method for evaluating the in vitro sun protection factor marketed by IN VITRO INTERNATIONAL (Irvine, Calif., USA).

A cosmetic base containing 10% by weight of the above extract was compared with the same base containing 10% by weight of pure propylene glycol. After applying the SOLATEX procedure, the following results were obtained:

base+propylene glycol → SPF=1
base+extract of the invention → SPF=4.5

The extract of the invention therefore proves effective for protecting the skin against ultraviolet radiation; the extract can be used alone or in combination with synthetic chemical screening agents or inorganic screening agents, increasing their efficacy.

Moreover, the following in vitro activity tests show the benefit of the extract obtained according to the invention in protecting the skin at the molecular level.

Anti-Free Radical Activity (determined according to V. Ponti, M. U. Dianzani, K. Cheeseman and T. F. Slater, Cehm—Biol interaction, 23 (1978) 281–291).

Superoxide anions are generated by the reaction of NADH (Nicotinamide Adenine Dinucleotide in a reduced form) with PMS (Phenazine Methosulphate). The superoxide anions reduce NBT (Nitro Blue Tetrazolium) to diformazan which is violet-blue in colour.

Figure 3A:
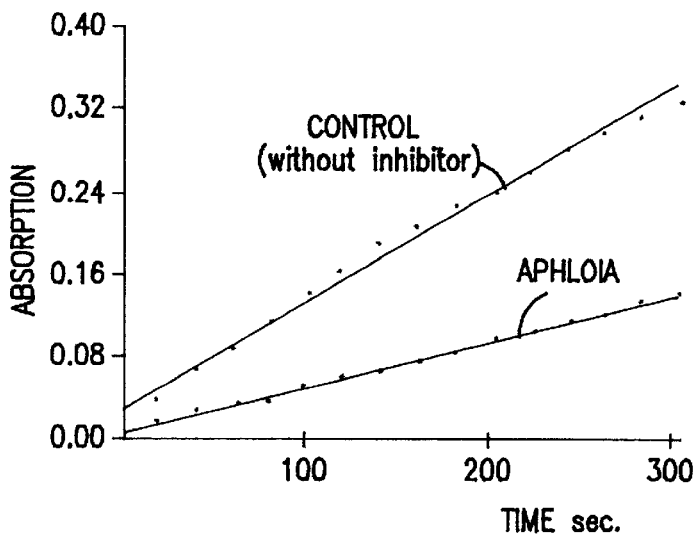
FIG. 3a represents the anti-free radical activity curves for an Aphloia extract and an inhibitor-free control as a function of time.

The appearance of reduced NBT is monitored over time using a spectrophotometer. The results are represented in FIG. 3a.

The anti-free radical activity of the extracts is expressed as rutin equivalent for a 50% inhibition. An Aphloia extract (1% dry extract) exhibits an activity 6 to 12 times higher than the rutin control (0.1%) depending on the polarity of the extraction solvent used.

The efficacy of the extracts considered in the protection relative to the superoxide radicals is quite significant.

Taking into account the active part of the free radicals in the ageing process, the Aphloia extract has potentially a beneficial activity in protecting the skin against ageing due to the alteration of the molecular structures of the epidermis.

Moreover, the Aphloia extracts have a protective activity relative to the structure of proteins: elastin and collagen.

Determination of the Anti-Elastase Activity (determined according to J. Bieth, B. Spices and Camille G. Wermecth, Biochemical medicine 11, 350–357, 1974, modified).

Figure 4A:
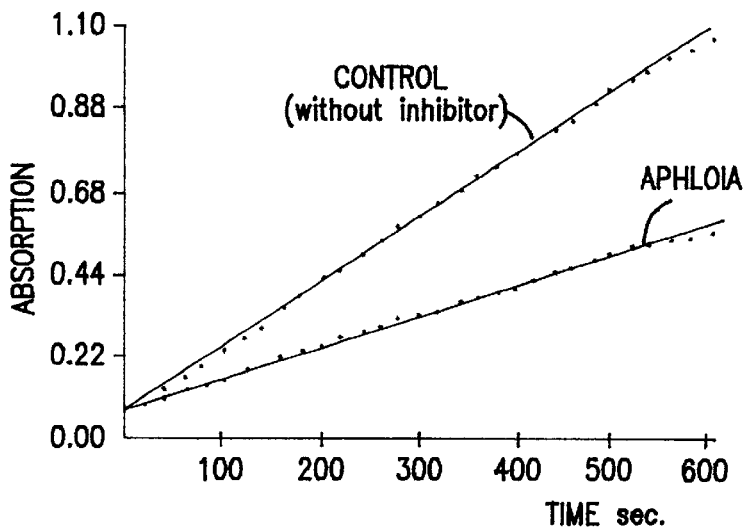
FIG. 4a represents the anti-elastase activity curves for an Aphloia extract and an inhibitor-free control (0.20%, ⅕ dil.)

A pancreatic elastase is reacted with a hydrophilic substrate, specific for the enzyme MeO Suc-Ala-Ala-Pro-Val-pNa and having the characteristic of liberating a chromogenic product, p-nitroanilide (pNa). The enzyme kinetics is monitored using a spectrophotometer. The results are presented in FIG. 4a.

The anti-elastase activity is expressed in arbitrary unit and is defined by the reciprocal of the quantity of extract for obtaining a 50% inhibition, multiplied by 100.

Thus 200 µl of the above extract, diluted ⅕, make it possible to obtain 50% inhibition compared with the inhibitor-free control. The activity is therefore $$\frac{1}{200} \times 100 \times 5 = 2.5$$

The Aphloia extract (1% dry extract) has an activity of 1 to 6 arbitrary units.

Anti-Collagenase Activity (determined according to Erich Wünsels and Hans Georg Heidrich 15.07.1963).

A *Clostridium histolycum* collagenase is reacted with a hydrophilic substrate (p. phenylazo-benzylcarbonyl-L propyl-L leucyl-glycyl-L Propyl-D arginine). The product resulting from the cut between Leu and Gly is lipophilic and absorbs UV light at 320 nm.

The anti-collagenase activity is expressed in arbitrary units and corresponds to the reciprocal of the quantity of extract (1% dry extract) necessary to obtain 50% inhibition multiplied by 100. For the Aphloia extract, the activity is from 0.5 to 3.

Anti-Hyaluronidase Activity (determined according to José L. Reissig, Jack L. Stominger and Luis F. Leloior, 05.12.1955).

The N-acetylglucosamine liberated after 45 minutes during the reaction of the hyaluronidase with hyaluronic acid is measured using a spectrophotometer. A process for reducing the anhydrous sugars, which in acid medium are converted to furan derivatives, is used; the said sugars react with para-dimethylaminobenzaldehyde to form a coloured complex.

The activity is expressed in µg of N-acetylglucosamine formed per minute.

The anti-hyaluronidase activity is expressed as a quantity of extract for obtaining 50% inhibition.

Figure 5A:
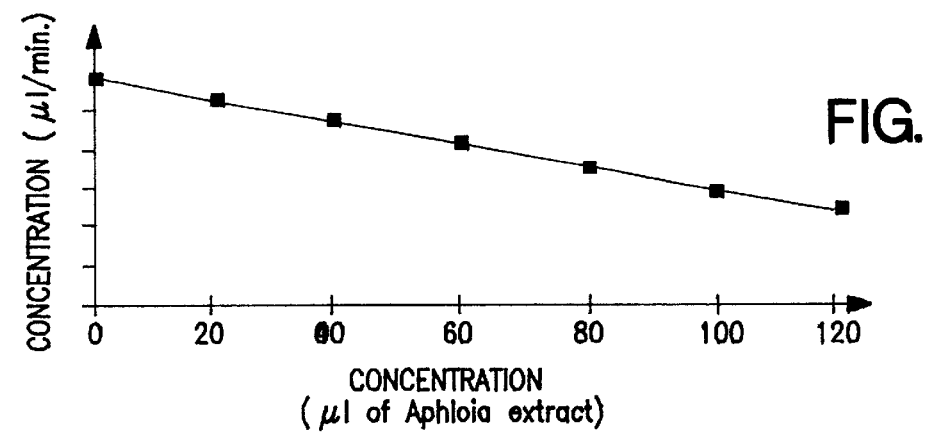
FIG. 5a represents the anti-hyaluronidase activity of an Aphloia extract.

The results are expressed in FIG. 5a.

The half-inhibition volume, $IV_{50}$, of the Aphloia extract is 95 to 120 µl. By way of comparison, heparin, a recognized inhibitor of hyaluronidase (Sigma 10 USP/ml) has an $IV_{50}$ of 380 µl.

Anti-Tyrosinase Activity (determined according to the modified method of Hamada, T and Mishima, Y(1972) British Journal of Dermatology, 86, 385).

Figure 6:
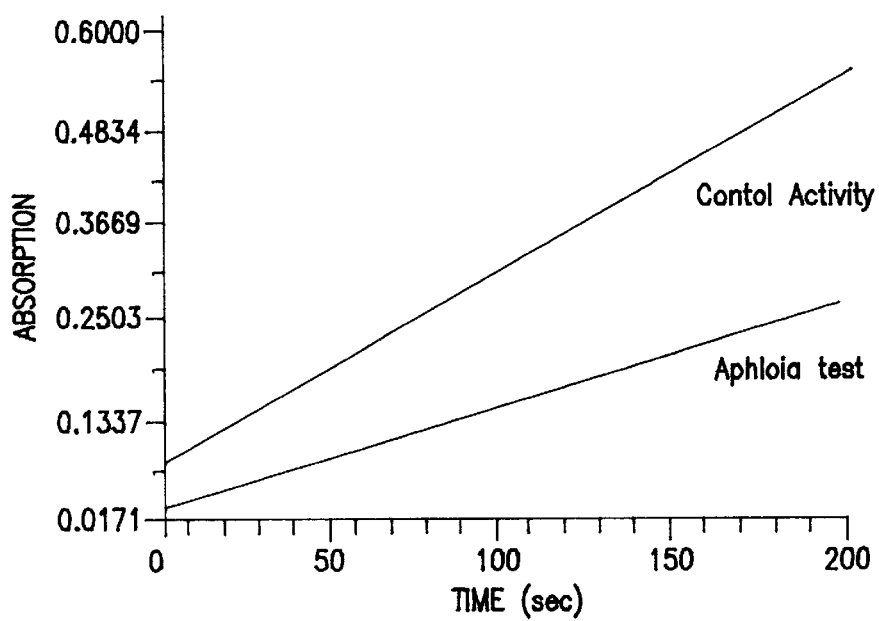
FIG. 6 represents the anti-tyrosinase activity of an Aphloia extract.

In this technique, the dopamine is brought into contact with a tyrosinase in a medium buffered at pH 7 and converted to dopachrome. Dopachrome is a coloured molecule which absorbs at 475 nm. The formation of the product is thus monitored over time at 475 nm (see FIG. 6).

The tyrosinase activity is indicated by the rate of formation of the product. The concentration of dry extract which is sufficient to reduce the rate by 50% ($IC_{50}$) is determined.

The $IC_{50}$ determined is of the order of $5 \times 10^{-2}$–0.3 mg/ml. This represents an activity 10 to 15 times higher than that obtained with a bearberry extract, already known for its anti-tyrosinase activity.

This data makes it possible to conclude that the Aphloia extract has a highly beneficial anti-tyrosinase activity. Consequently, in addition to the uses already defined, the extracts can therefore be used in treatment and/or decorative cosmetics and in pharmacy, to help the resorption of brown spots due to skin ageing and more generally to skin whitening.

The Aphloia extracts possess quite a considerable protective effect against molecular damage of the skin which makes it possible to envisage their application as cosmetic product, in particular for protecting the skin and the hair against ultraviolet rays, for combatting age-related skin ageing and in general for enhancing the appearance and the quality of the structure of the epidermis.

II—MANGIFERA EXTRACTS

The Mangifera extract is obtained from any Mangifera species, and in particular *Mangifera indica* L.

The principal constituents currently identified in the extract of Mangifera sp. leaves of the invention are:

A C-glucosyltetrahydroxyxanthan
Flavonoids

Tannins
(It is free of alkaloid substances).

The Mangifera extract is obtained in the same manner as the Aphloia extract, by subjecting the fresh or dry leaves to extraction by a polar solvent or a mixture of polar solvents (alkanol/water or propylene glycol/water for example). These extracts can be used in liquid form, concentrated to a greater or lesser degree or in dry form.

Example of Mancifera Extract

The extract studied was obtained in the following manner:

5% (w/w) of dry leaves from *Mangifera indica*, coarsely ground, are brought into contact, with stirring and at 50° C., with an ethanol/water mixture (30/70). The extraction takes place for 1 h 30 min. The plant is separated by filtration on a cloth (55 µm). The extract is then filtered on a cellulose filter (5 µm).

Photoprotective Effect

Figure 1B:
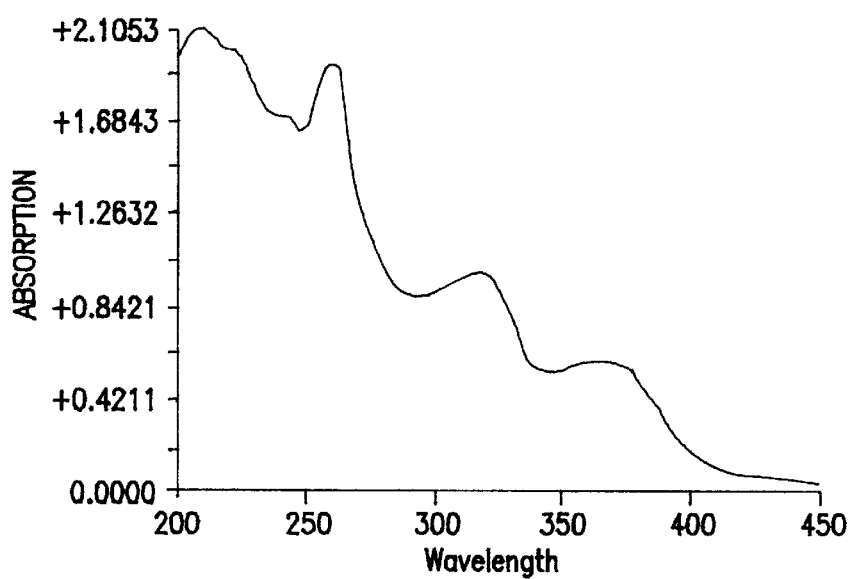
FIG. 1b represents the UV light absorption spectrum as a function of the wavelength for a Mangifera extract.

The Mangifera extract described above exhibits an absorption spectrum in the UV region which is very useful for an application for protecting against solar erythema, with a maximum at around 320 nm, corresponding to UVB rays and another at around 360 nm, corresponding to the zone of UVA rays, as represented in Figure 1b.

Moreover, the absence of phototoxicity was verified.

Taking into account its safety, the resistance of the extract to irradiation (its photostability) was tested relative to those of synthetic screening agents already marketed (such as for example benzophenone 3, GAF, USA or UVINUL T150, BASF, Germany) in solvents compatible with their respective solubilities.

The extract was therefore subjected to a continuous radiation whose spectrum is comparable to that of sunlight and has a controllable energy level, emitted by a xenon lamp. The variation of the absorption spectrum was monitored over time and the half-life time measured (duration of irradiation necessary for a 50% loss of absorption at a fixed wavelength).

Figure 2B:
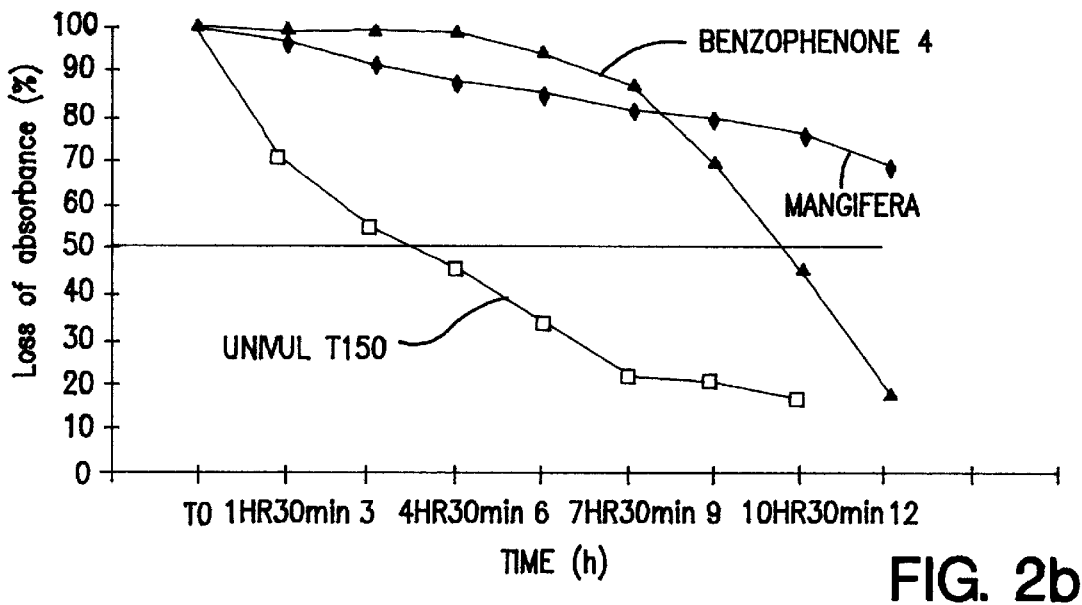
FIG. 2b represents the photostability as a function of time for a Mangifera extract, compared with two commercially available synthetic sunscreens (Mangifera extract, Univul T150, benzophenone 3)

As represented in FIG. 2b, the Mangifera extract, compared with benzophenone 3, and with UVINUL T150 under the same conditions, proved at least equally resistant to irradiation, with a half-life time considerably greater than these two synthetic screening agents.

Finally, the Mangifera extract prepared as described in the process according to the invention was tested in a cosmetic composition in order to evaluate its protection value SPF, according to the SOLATEX method, a method for evaluating the in vitro sun protection factor marketed by IN VITRO INTERNATIONAL (Irvine, Calif., USA).

5% by weight of the above extract was incorporated into a cosmetic base (containing, in addition, 1.5% Parsol 1789, 4% Parsol MCX, 2% Eusolex 507 and 2% fine titanium oxide Tioveil, conferring on it an initial SPF equal to 8). This preparation was compared with the same base containing 5% by weight of pure propylene glycol. After applying the SOLATEX procedure, the following results were obtained:

base alone → SPF=8 base+extract of the invention → SPF=14

The extract of the invention therefore proves effective for protecting the skin against ultraviolet radiation; the extract can be used alone or in combination with synthetic chemical screening agents or inorganic screening agents, increasing their efficacy.

The benefit of the extract obtained according to the invention for protecting the skin at the molecular level is also illustrated by the following examples:

Anti-Free Radical Activity Determined in vitro (V. Ponti, M. U. Dianzani, K. Cheeseman and T. F. Slater, Chem. Biol. interaction, 23, 281–291, 1978).

Figure 3B:
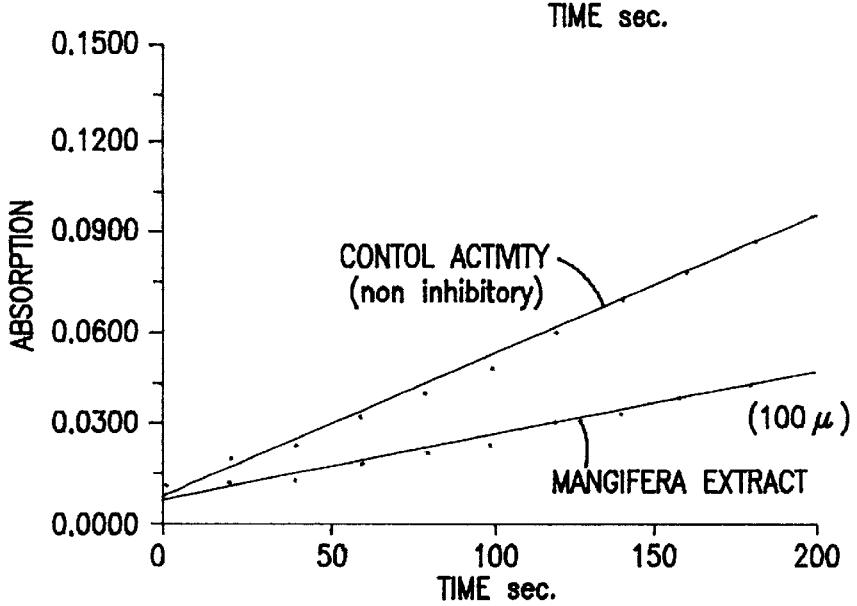
FIG. 3b represents the anti-free radical activity curves for a Mangifera extract (0.25% dry ext.) and an inhibitor-free control as a function of time.

The technique used is the same as that described for the Aphloia extract. The results are presented in FIG. 3b.

The anti-free radical activity of the extracts is expressed as rutin equivalent for a 50% inhibition. A Mangifera extract (1% dry extract) exhibits an activity 15 to 30 times higher than the rutin control (0.1%) depending on the polarity of the extraction solvent used.

The data obtained show that the efficacy of the extracts considered in the protection relative to the superoxide radicals is quite significant.

The free radicals being known for their significant active part in the ageing process, the extract according to the invention therefore potentially has a beneficial activity in protecting the skin against ageing due to alteration of the molecular structures of the epidermis.

Anti-Elastase Activity Determined in vitro (J. Bieth, B. Spices and Camille G. Wermecth, Biochemical medicine 11, 350–357, 1974, modified).

The procedure followed is the same as that described for the Aphloia extract.

Figure 4B:
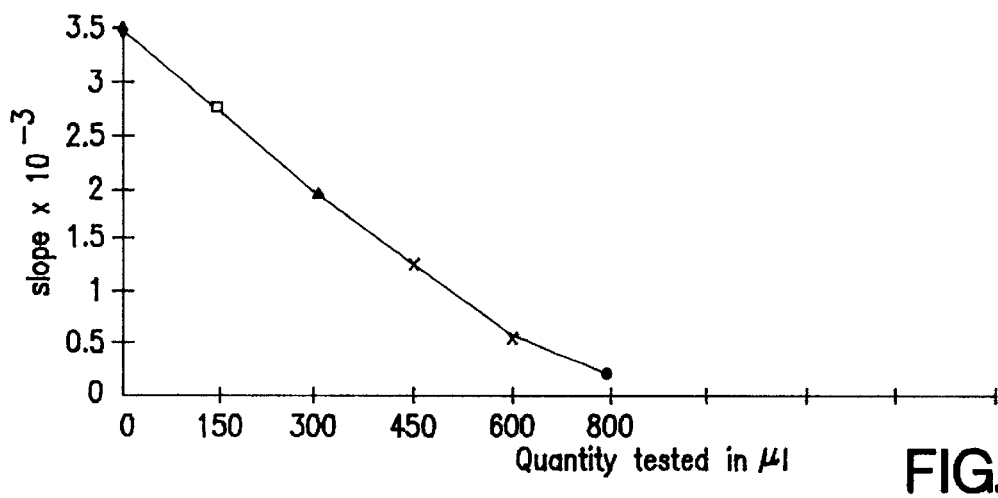
FIG. 4b represents the anti-elastase activity curve for a Mangifera extract (0.25%, ¼ dil.) determined by enzyme kinetics using a spectrophotometer (measurement of the ratio of the absorbance to the time)

The curve of the slopes obtained as a function of the quantities of Mangifera extract thus makes it possible to define the concentration corresponding to 50% inhibition ($IC_{50}$). This curve is plotted in FIG. 4b.

The Mangifera extract according to the invention exhibits a very significant $IC_{50}$, of the order of $5 \times 10^{-2}$–1 mg/ml which may go above this range depending on the species considered.

Anti-Collagenase Activity Determined in vitro (Erich Wünsch and Hans Georg Heidrich Hoppe-Seyler's—Zeit—Physiol.—Chem. 333, 149–151, 1963).

A collagenase is reacted with a hydrophilic substrate (p. phenylazo-benzylcarbonyl-L propyl-L leucyl-glycyl-L Propyl-D arginine). The product resulting from the cut between Leu and Gly is lipophilic and absorbs UV light at 320 nm.

The inhibitory effect of Mangifera is measured by adding the extract obtained according to the invention to the reaction medium.

Figure 7A:
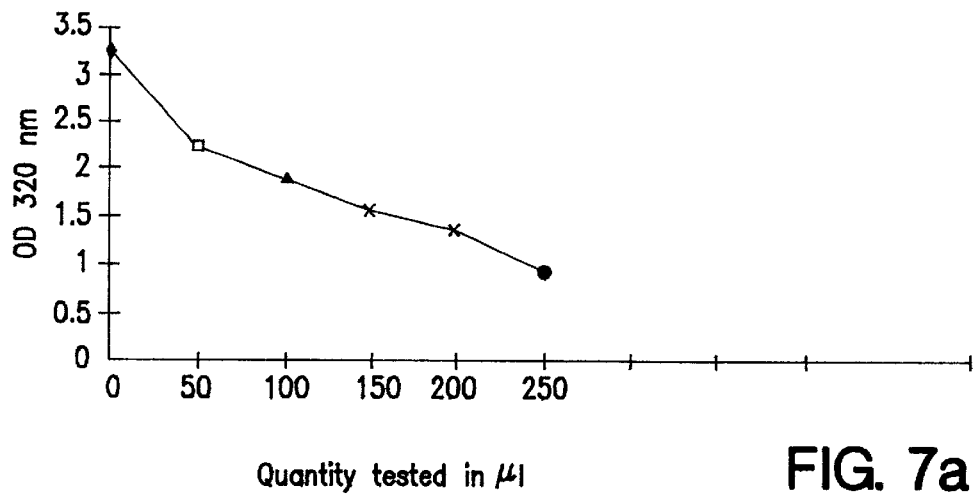
FIG. 7a represents the anti-collagenase activity curve for a Mangifera extract (0.25%) determined by measurement of the optical density at 320 nm.

FIG. 7a represents the curve for the values obtained at 320 nm as a function of the various volumes of Mangifera extract added to the medium.

The concentration allowing 50% inhibition ($IC_{50}$) can thus be determined.

The Mangifera extract exhibits an $IC_{50}$ of the order of $5 \times 10^{-2}$–1 mg/ml and may go above this range depending on the species considered.

Anti-Hyaluronidase Activity Determined in vitro (José L. Reissig, Jack L. Strominger and Luis F. Leloir, J. Biol.—Chem. 217, 960–966, 1953).

The procedure is the same as that described for the Aphloia extract.

The activity is expressed in µg of N-acetylglucosamine formed per minute.

Figure 5B:
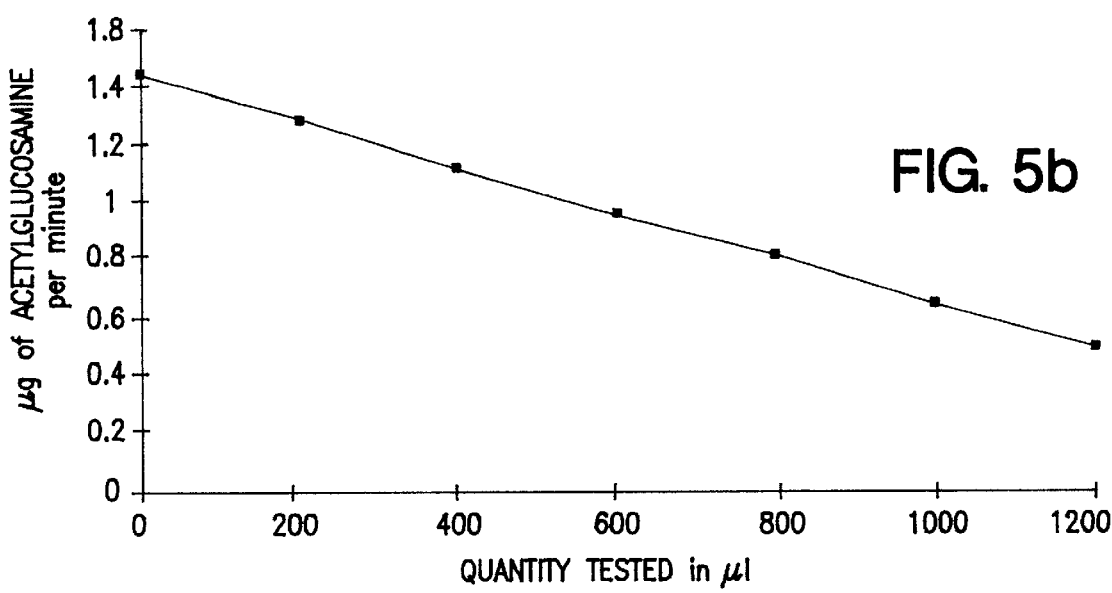
FIG. 5b represents the anti-hyaluronidase activity of a Mangifera extract (0.25%)

The anti-hyaluronidase activity is expressed as quantity of extract for obtaining 50% inhibition. The results are plotted in Figure 5b.

The half-inhibition volume of the Mangifera extract (1% dry extract) $IV_{50}$ is 200–250 µl compared with heparine, a recognized hyaluronidase inhibitor (Sigma 10 USP/ml) whose $IV_{50}$=380 µl.

Anti-Tyrosinase Activity (determined according to the modified method of Hamada, T and Mishima, Y (1972) British Journal of Dermatology, 86, 385).

The procedure followed is the same as that described for the Aphloia extract. The tyrosinase activity is indicated by the rate of formation of the product, measured at 475 nm.

The concentration of dry extract which is sufficient to reduce the rate by 50% is determined: $IC_{50}$ of the order of 2 to 3 mg/ml.

This data make it possible to conclude that the Mangifera extract possess a protective effect against molecular damage on the skin which is quite considerable and, consequently, their use in cosmetics has an obvious benefit, in particular for protecting the skin and the hair against ultraviolet rays, for combatting age-related skin ageing and in general for enhancing the appearance and the quality of the structure of the epidermis.

III—PURIFIED MANGIFERINE

Example of Preparation of a Mangiferine Solution From a Plant Extract

One of the processes for extracting mangiferine consists in extracting, with 40% ethanol, the glucosides of the xanthone of the ground plant of the genus *Mangifera indica*. The extraction is carried out with the use of heat (for example 50° C.), at the rate of 1 kg of plant material per 10 l of extracting agent. The extract is partially evaporated and cooled. The mangiferine crystallizes and precipitates. This precipitate is recovered and it is rinsed several times with a mixture of solvents, such as water or chloroform, until the purified substance is obtained.

Photoprotective Effect

Figure 1C:
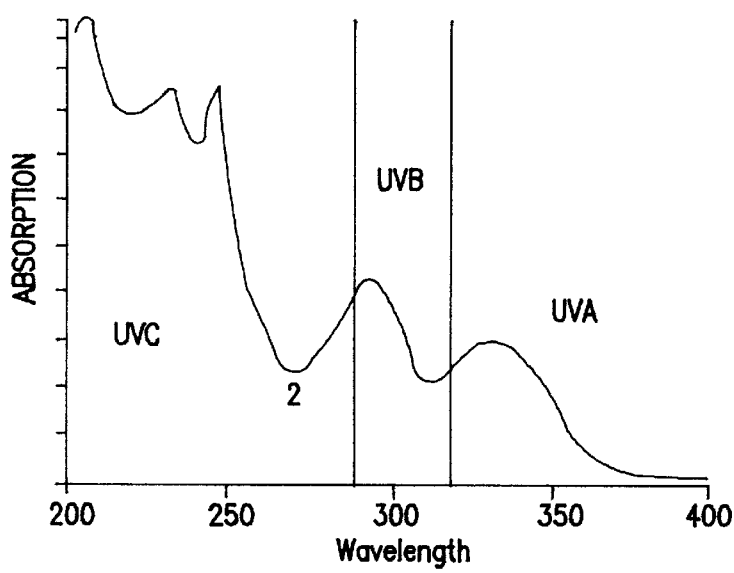
FIG. 1c represents the UV light absorption spectrum as a function of the wavelength for mangiferine.

Mangiferine (or its derivatives) exhibits an absorption spectrum in the UV region which is very useful for an application for protecting against solar erythema, with a maximum at around 320 nm, corresponding to UVB rays and another at around 360 nm, corresponding to the zone of UVA rays, as represented in Figure 1c.

Moreover, the absence of phototoxicity was verified.

Taking into account its safety, the resistance of the extract to irradiation (its photostability) was tested relative to those of synthetic screening agents already marketed (such as for example octylmethoxycinnamate, Parsol MCX, Givaudan, Basle, Switzerland).

A mangiferine solution was subjected to a continuous radiation whose spectrum is comparable to that of sunlight and has a controllable energy level, emitted by a xenon lamp. The variation of the absorption spectrum was monitored over time and the half-life time measured (duration of irradiation necessary for a 50% loss of absorption at a fixed wavelength).

Figure 2C:
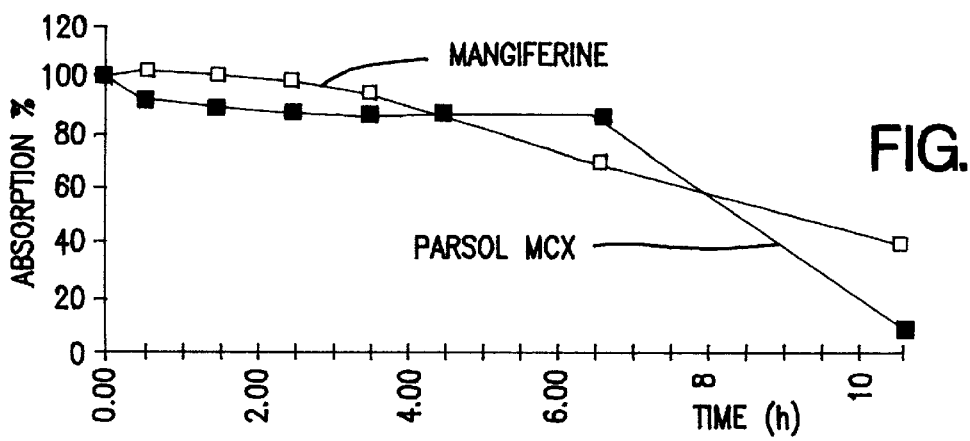
FIG. 2c represents the photostability as a function of time for mangiferine compared with a commercially available sunscreen (Parsol MCX)

As represented in FIG. 2c, the aqueous mangiferine solution, compared with benzophenone 4 under the same conditions, proved equally resistant to irradiation, with a very similar half-life time.

Furthermore, its calculated molecular absorption coefficient proved similar to those of most synthetic screening agents marketed, that is to say between 20 000 and 30 000 $L.cm^{-1}.mole^{-1}$.

Mangiferine may therefore prove effective for protecting the skin against ultraviolet radiation; it can be used alone or in combination with synthetic chemical screening agents or inorganic screening agents, increasing their efficacy.

The benefit of mangiferine for protecting the skin at the molecular level is also illustrated by the following examples:

Anti-Elastase Activity Determined in vitro (J. Bieth, B. spices and Camille G. Wermecht, Biochemical medicine 11, 350–357, 1974) modified.

According to the same procedure as that described above for the Aphloia and Mangifera extracts, increasing quantities of a mangiferine solution (0.01%) are introduced into a final reaction mixture of 3.01 ml.

Figure 4C:
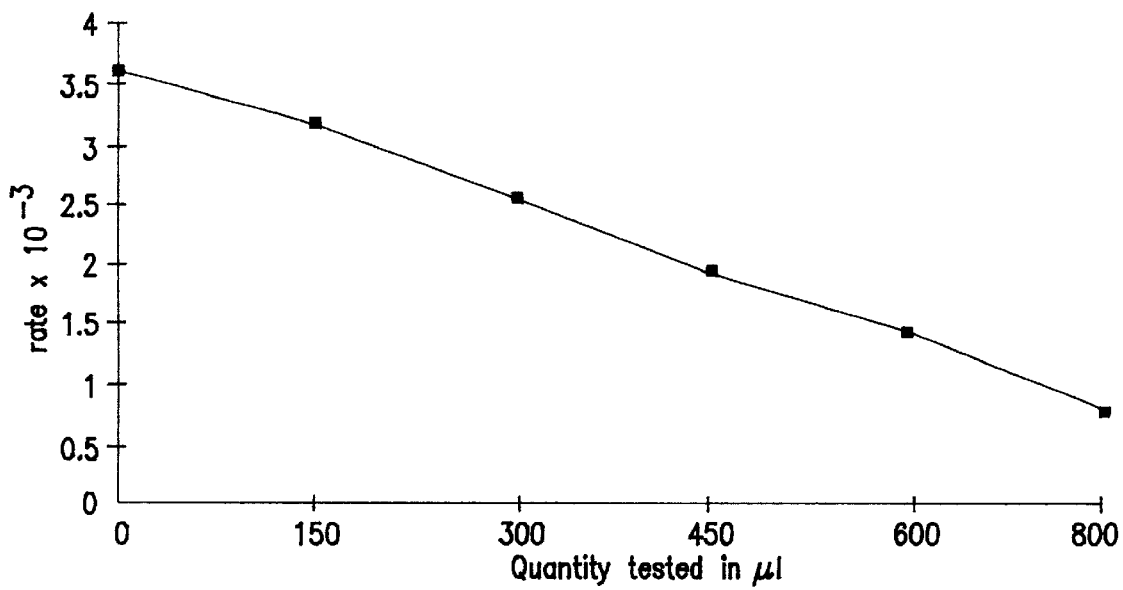
FIG. 4c represents the anti-elastase activity curve for mangiferine (0.01%)

The curve of the slopes obtained as a function of the quantities of mangiferine thus makes it possible to define the concentration corresponding to 50% inhibition ($IC_{50}$). This curve is plotted in FIG. 4c.

Mangiferine exhibits a very significant $IC_{50}$ of the order of $10^{-2}$ mg/ml.

Anti-Collagenase Activity Ddetermined in vitro (Erich Wünsch and Hans Georg Heidrich Hoppe-Seyler's—Zeit—Physiol. Chem. 333, 149–151, 1963).

The inhibitory effect of mangiferine is measured by adding to the reaction medium a solution at 0.042% in propylene glycol.

Figure 7B:
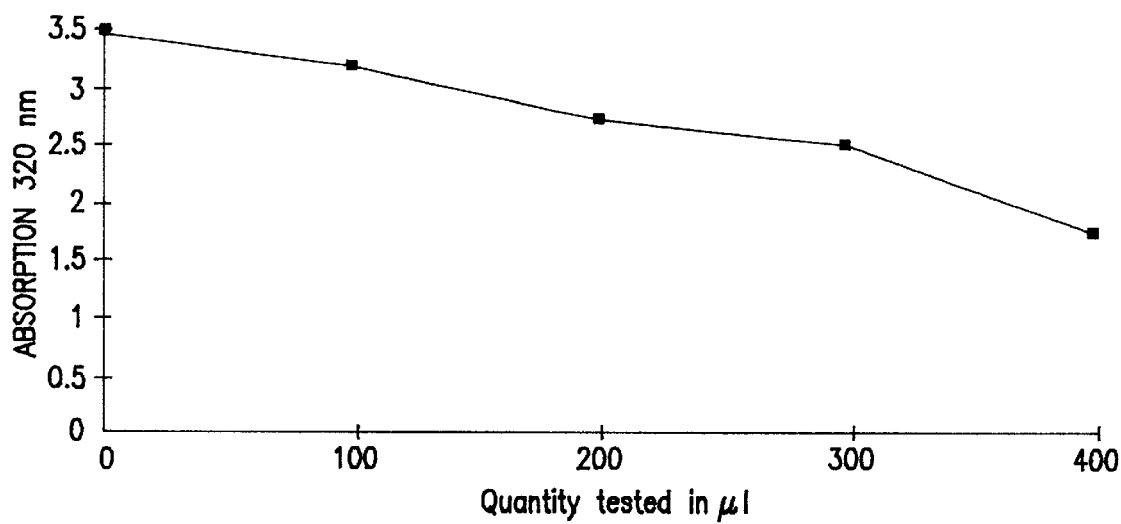
FIG. 7b represents the anti-collagenase activity curve for mangiferine (0.042%).

FIG. 7b represents the curve of the values obtained at 320 nm as a function of the various volumes of mangiferine solution which are added to the medium. The concentration allowing 50% inhibition ($IC_{50}$) can thus be determined. Mangiferine has an $IC_{50}$ of the order of $5 \times 10^{-2}$ mg/ml.

The data obtained shows that the efficacy of this molecule, in particular in relation to protecting the structural qualities of the skin, is quite significant.

Anti-Tyrosinase Activity in vitro

A tyrosinase is reacted at room temperature with a substrate L-Dopa. The product formed is monitored over time using a spectrophotometer at 475 nm. A 0.2% mangiferine solution allows a 50% inhibition of the tyrosinase, that is to say an $IC_{50}$ of the order of 0.2 mg/ml.

By its anti-tyrosinase effect, mangiferine may contribute to the unification of the appearance of the skin.

Anti-Free Radical Activity Determined in vitro (V. Ponti, M. U. Dianzani, K. Cheeseman and T. F. Slater, Chem. Biol. interaction, 23, 281–291, 1978).

Figure 3C:
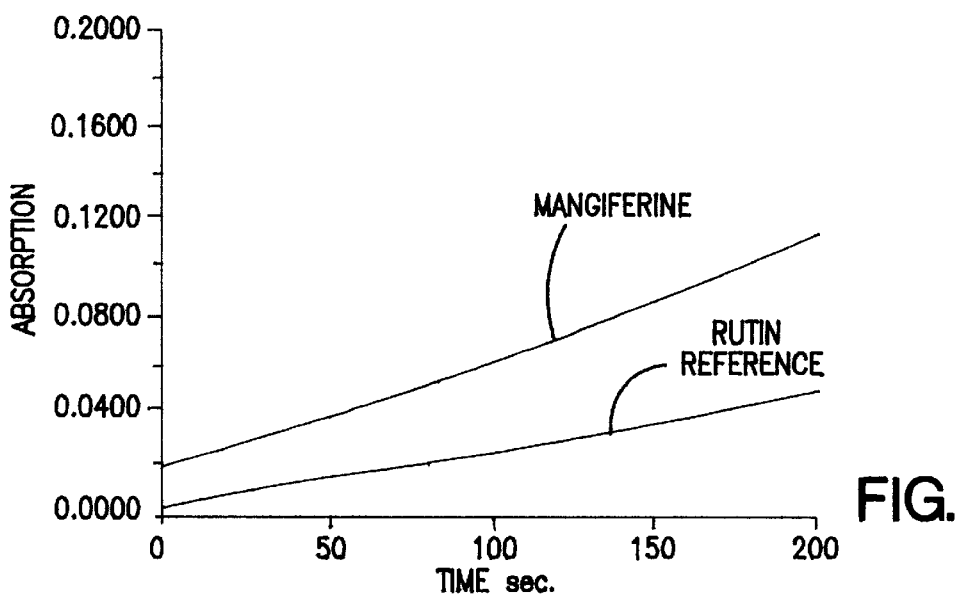
FIG. 3c represents the anti-free radical activity curves for mangiferine (0.05%) and an inhibitor-free control as a function of time.

The results are presented in FIG. 3c.

The anti-free radical activity of the extracts is expressed in rutin equivalent for a 50% inhibition.

A 1% mangiferine solution in propylene glycol exhibits an activity 4 times higher than a 0.1% rutin reference solution. The data obtained shows that the efficacy of this molecule in protecting against superoxide radicals is beneficial.

All this data makes it possible to conclude that the mangiferine molecule or its derivatives, as well as the Aphloia or Mangifera extracts containing it, can be used in treatment and/or decorative cosmetics and in pharmacy. They are in particular useful: for protecting against UVA and UVB radiation, by virtue of their screening and anti-free radical role, protecting from the harmful effect of the radicals produced under the effect of UVA radiation; for skins made fragile by time (age): reduction of the hydration and tonus of the tissues, by virtue of their anti-hyaluronidase properties which limit the degradation of hyaluronic acid (proteoglycan having a very potent hydrating power); as well as of their anti-collagenase and anti-elastase properties which limit the degradation of collagen and of elastin, the state of these molecules being especially responsible for the structural quality of the skin.

The extracts of Aphloia and Mangifera sp. leaves as well as mangiferine in a pure form and its derivatives can be used as they are, vectorized, microencapsulated, in combination with a mixture of excipients such as: plant or mineral oils; plant or mineral waxes; silicones; alcohols and fatty acids; surfactants; derivatives of proteins, inorganic or organic gelling agents; lanolin and its derivatives; organic or inorganic UV-screening agents, water; or in combination with other plant extracts.

The following examples of composition containing an extract of Aphloia, of Mangifera or of purified mangiferine as active ingredient illustrate the present invention.

1. Examples of Compositions in the Form of Gels

The following tables indicate the formulations for compositions in the form of an aqueous gel (column 1) or of an aqueous-alcoholic gel (column 2), containing purified mangiferine:

|  | (1) | (2) |
|---|---|---|
| Polyacrylic acid | 1.20 | 1.20 |
| Xanthan gum | 0.30 | 0.30 |
| Mangiferine | 0.01 to 10% | 0.01 to 10% |
| Water | qs | qs |
| Ethanol | x | 50 |
| Triglycerides C8/C10 | 5 | x |
| Lanolin 78 EO * | x | 5 |
| Oleyl alcohol 200 E | 3 | x |
| Perfume | 0.20 | 0.20 |
| Triethanolamine (TEA) | 1.10 | 1.10 |

* Ethoxylated lanolin with 78 moles of EO containing a Mangifera extract:

|  | (1) | (2) |
|---|---|---|
| Polyacrylic acid | 1.20 | 1.20 |
| Hydroxypropyl | 0.20 | 0.20 |
| Dry extract of Mangifera | 0.01 to 10% | 0.01 to 10% |
| Water | qs | qs |
| Ethanol | x | 40 |
| Capric acid 7 EO ** | 3 | x |
| Dimethicone copolyol | x | 5 |
| Lauryl alcohol 14 EO *** | 3 | x |
| Perfume | 0.20 | 0.20 |
| NaOH | 0.30 | 0.35 |

** Ethoxylated capric acid with 7 moles of EO
*** Ethoxylated lauryl alcohol with 14 moles of EO 2. Examples of Compositions in the Form of an Emulsion containing purified mangiferine:

|  |  |  |
|---|---|---|
| A | Water | qs |
|  | Mangiferine | 0.01 to 10% |
|  | Preservatives | qs |
|  | Propylene glycol | 5.00% |
|  | Xanthan gum | 0.30% |
|  | Acrylic/acrylate copolymer | 0.50% |
|  | Stearic acid 100 EO **** | 3.00% |
|  | Sorbitan stearate | 2.00% |
|  | Sorbitan laurate 20 EO | 3.00% |
|  | Cetylstearyl alcohol | 1.50% |
| B | Beeswax | 1.00% |
|  | Wheat germ oil | 5.00% |
|  | Dimethicone | 2.00% |
|  | Cyclomethicone | 5.00% |
| C | Polyacrylamide gel | 2.00% |
| D | Perfume | 0.30% |

**** Ethoxylated stearic acid with 100 moles of EO containing an Aphloia extract:

|  |  |  |
|---|---|---|
| A | Water | qs |
|  | Dry extract of Aphloia | 0.01 to 10% |
|  | Preservatives | qs |
|  | Dipropylene glycol | 5.00% |
|  | Sodium alginate | 0.30% |
|  | Acrylic/acrylate copolymer | 0.50% |
|  | Stearic acid 100 EO | 3.00% |
|  | Sorbitan stearate | 2.00% |
|  | Sorbitan laurate 20 EO | 3.00% |
|  | Stearic acid | 1.50% |
| B | Carnauba wax | 1.00% |
|  | Hazelnut oil | 5.00% |
|  | Dimethicone | 2.00% |
|  | Cyclomethicone | 5.00% |
| C | Polyacrylamide gel | 2.00% |
| D | Perfume | 0.30% |

3. Examples of Compositions in the Form of a Cream containing purified mangiferine

|  |  |  |
|---|---|---|
|  | Water | qs |
|  | Xanthan gum | 0.30% |
| A | Sequestrant (for ex. EDTA) | 0.05% |
|  | Preservatives | qs |
|  | Mangiferine | 0.01 to 10% |
|  | C 18 acid | 2.50% |
|  | C 16 alcohol | 2.50% |
|  | Trilaurine | 1.00% |
| B | Shea butter | 3.00% |
|  | Tocopherol acetate | 0.05% |
|  | α-bisabolol | 0.05% |
|  | Vegetable oil (wheat) | 5.00% |
|  | Dimethicone | 3.00% |
|  | Polyacrylic acid | 0.30% |
| C | Water | 3.00% |
| D | TEA | 1.50% |
| E | Perfume | 0.10% | containing a Mangifera extract:

|  |  |  |
|---|---|---|
|  | Water | qs |
|  | Guar gum | 0.30% |
| A | Sequestrant (for ex. EDTA) | 0.05% |
|  | Preservatives | qs |
|  | Mango dry extract | 0.01 to 10% |
|  | C 18 acid | 2.50% |
|  | Cetyl palmitate | 2.50% |
|  | Trilaurine | 1.00% |
| B | Shea butter | 3.00% |
|  | tocopherol acetate | 0.05% |
|  | α-bisabolol | 0.05% |
|  | Ethyl hexyl cocoate | 5.00% |
|  | Dimethicone | 3.00% |
|  | Polyacrylic acid | 0.30% |
| C | Water | 3.00% |
| D | TEA | 1.50% |
| E | Perfume | 0.10% |

4. Examples of Compositions in the Form of a Lotion containing purified mangiferine

|  |  |
|---|---|
| Water | qs |
| Sequestrant | 0.05% |
| Propylene glycol | 2.00% |
| Preservatives | qs |
| Mangiferine | 0.01 to 10% |
| Alcohol | 5 to 50% |
| Oleyl alcohol 20 EO | 1.00% |
| Perfume | 0.05% |
| Colorants | qs | containing an Aphloia extract:

|  |  |
|---|---|
| Water | qs |
| Sequestrant | 0.05% |
| Methyl gluceth 20 (emollient) | 2.00% |
| Preservatives | qs |
| Aphloia extract | 0.01 to 50% |
| Alcohol | 5 to 50% |
| Castor oil 40 EO | 1.00% |
| Perfume | 0.05% |
| Colorants | qs |
| Allanthoin | 0.1% |

We claim:

1. A method of cosmetic treatment, which comprises applying to the skin, lips or the hair an effective amount of a cosmetic composition comprising a compound of the following general formula I:

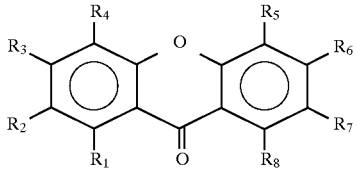

Formula I where $R_1, R_2, R_3, R_4, R_5, R_6, R_7, R_8$ are selected from the group consisting of —H, —OH, —OCH$_3$, and a glucosyl radical or one of its pharmaceutically acceptable salts, in admixture with a topically acceptable carrier.

2. A method of cosmetic treatment according to claim 1, in which $R_1$, $R_3$, $R_6$, $R_7$ are selected from the group consisting of —H, —OH, —OCH$_3$, and a glucosyl radical and $R_2$=$R_5$=$R_8$=—H and $R_4$ is a glucosyl radical, or $R_2$ is a glucosyl radical and $R_4$=$R_5$=$R_8$=—H.

3. A method of cosmetic treatment according to claim 1, in which $R_1$=$R_3$=$R_6$=—OH and $R_2$ is a glucosyl radical and $R_4$=$R_5$=$R_6$=—H.

4. A method of cosmetic treatment according to claim 1, wherein the compound is present in a quantity of 0.01 to 50% by weight, in a dry form.

5. A method of cosmetic treatment according to claim 1, wherein the compound is present in a quantity of 0.01 to 10% by weight, in a dry form.

6. A method of cosmetic treatment according to claim 1, wherein the compound is present in the form of a plant extract, obtained by extraction with a polar solvent or a mixture of polar solvents.

7. A method of cosmetic treatment according to claim 6, wherein compound is present in the form of an extract of Aphloia leaves.

8. A method of cosmetic treatment according to claim 6, wherein the compound is present in the form of an extract of Mangifera leaves.

9. A method of cosmetic treatment according to claim 7, wherein said extract of leaves is present in a quantity from 0.01 to 20%, expressed by weight of dry extract relative to the total weight of the composition.

10. A method of cosmetic treatment according to claim 6, wherein the plant extract is obtained by extraction with a polar solvent or a mixture of polar solvents selected from the group consisting of water, alkanol, propylene glycol and butylene glycol.

11. A method of cosmetic treatment according to claim 1, wherein said composition is present in the form of simple or multiple emulsions, of a microemulsion, of aqueous or aqueous-alcoholic gels, of a cream, of oils, of aqueous or aqueous-alcoholic lotions, of a stick, of a shampoo or conditioner.

12. A method for protecting the skin, the lips or the hair against ultraviolet rays, wherein a cosmetic composition comprising a compound of the following general formula I:

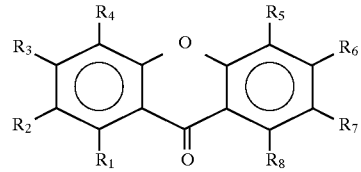

Formula I where $R_1, R_2, R_3, R_4, R_5, R_6, R_7, R_8$ are selected from the group consisting of —H, —OH, —OCH$_3$, and a glucosyl radical or one of its pharmaceutically acceptable salts, is applied to the skin, the lips or the hair.

13. A method for enhancing the structural quality of the skin, which comprises applying to the skin an effective amount of a cosmetic composition comprising a compound of the following general formula I:

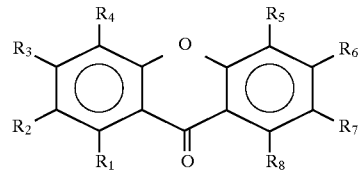

Formula I where $R_1, R_2, R_3, R_4, R_5, R_6, R_7, R_8$ are selected from the group consisting of —H, —OH, —OCH$_3$, and a glucosyl radical or one of its pharmaceutically acceptable salts, in admixture with a topically acceptable carrier.

* * * * *